United States Patent
Berkey et al.

(10) Patent No.: US 10,765,325 B2
(45) Date of Patent: Sep. 8, 2020

(54) PASSENGER COMFORT SYSTEM

(71) Applicant: The Boeing Company, Chicago, IL (US)

(72) Inventors: Tyler E. Berkey, Charleston, SC (US); Daniel S. Thomas, Summerville, SC (US)

(73) Assignee: The Boeing Company, Chicago, IL (US)

( * ) Notice: Subject to any disclaimer, the term of this patent is extended or adjusted under 35 U.S.C. 154(b) by 313 days.

(21) Appl. No.: 15/889,297

(22) Filed: Feb. 6, 2018

(65) Prior Publication Data
US 2019/0239757 A1    Aug. 8, 2019

(51) Int. Cl.
*G01C 23/00*    (2006.01)
*G05D 1/00*    (2006.01)
(Continued)

(52) U.S. Cl.
CPC ........ *A61B 5/02055* (2013.01); *A61B 5/0004* (2013.01); *A61B 5/14532* (2013.01);
(Continued)

(58) Field of Classification Search
CPC ... A61B 5/02055; A61B 5/7278; A61B 5/681; A61B 5/4809; A61B 5/4266;
(Continued)

(56) References Cited

U.S. PATENT DOCUMENTS

2008/0048101 A1  2/2008  Romig et al.
2013/0070043 A1* 3/2013  Geva ............... B60K 28/066
                                         348/14.02
(Continued)

FOREIGN PATENT DOCUMENTS

DE   102014208347 A1   11/2015
DE   102015221484 A1    5/2017
(Continued)

OTHER PUBLICATIONS

Extended European Search Report, dated Jul. 10, 2019, regarding Application No. 19155392.4, 11 pages.
(Continued)

*Primary Examiner* — Harry T Oh
(74) *Attorney, Agent, or Firm* — Yee & Associates, P.C.

(57) ABSTRACT

A method for managing passenger comfort. A passenger mobile device is connected with a vehicle computer system in a vehicle using a near-field communications reader for a passenger seat. Passenger comfort preferences associated with the passenger seat are identified by the vehicle computer system based on changes made to an environment in the vehicle by a passenger. Passenger comfort preferences made to the environment by the passenger are sent from the vehicle computer system to the passenger mobile device, which are associated with different current states. New comfort preferences are received by the vehicle computer system from the passenger mobile device when the passenger mobile device detects a change in a current state of the passenger. Signals are sent by the vehicle computer system to a number of vehicle systems to change the environment using the new comfort preferences, enabling an increase in the passenger comfort in the vehicle.

28 Claims, 10 Drawing Sheets

(51) Int. Cl.
  *G05D 3/00* (2006.01)
  *G06F 7/00* (2006.01)
  *G06F 17/00* (2019.01)
  *A61B 5/0205* (2006.01)
  *B64D 13/00* (2006.01)
  *B60Q 3/00* (2017.01)
  *B60R 16/037* (2006.01)
  *B64D 11/00* (2006.01)
  *B60H 1/00* (2006.01)
  *B60N 2/02* (2006.01)
  *B64D 11/06* (2006.01)
  *A61B 5/00* (2006.01)
  *A61B 5/145* (2006.01)
  *B64C 1/14* (2006.01)
  *A61B 5/021* (2006.01)
  *A61B 5/024* (2006.01)
  *A61B 5/08* (2006.01)

(52) U.S. Cl.
  CPC .......... *A61B 5/4266* (2013.01); *A61B 5/4809* (2013.01); *A61B 5/681* (2013.01); *A61B 5/7278* (2013.01); *B60H 1/00371* (2013.01); *B60H 1/00742* (2013.01); *B60N 2/0244* (2013.01); *B60Q 3/00* (2013.01); *B60R 16/037* (2013.01); *B64C 1/1484* (2013.01); *B64D 11/00* (2013.01); *B64D 11/0007* (2013.01); *B64D 11/0015* (2013.01); *B64D 11/00155* (2014.12); *B64D 11/064* (2014.12); *B64D 13/00* (2013.01); *A61B 5/021* (2013.01); *A61B 5/02438* (2013.01); *A61B 5/0816* (2013.01)

(58) Field of Classification Search
  CPC . A61B 5/14532; A61B 5/0004; A61B 5/0816; A61B 5/02438; A61B 5/021; B60N 2/0244; B60H 1/00742; B60H 1/00371; B64D 11/00; B64D 11/00155; B64D 11/0015; B64D 11/0007; B64D 11/064; B64D 13/00; B64C 1/1484; B60R 16/037; B60Q 3/47; B60Q 3/80; B60Q 3/00; H04W 4/80
  See application file for complete search history.

(56) References Cited

U.S. PATENT DOCUMENTS

| | | |
|---|---|---|
| 2013/0338857 A1 | 12/2013 | Sampigethaya |
| 2014/0125355 A1* | 5/2014 | Grant .................. B64D 11/062 324/629 |
| 2014/0229060 A1 | 8/2014 | MacNeille et al. |
| 2016/0107646 A1* | 4/2016 | Kolisetty ............. B60W 30/12 701/96 |
| 2018/0129655 A1* | 5/2018 | Geissinger .......... G06F 16/9038 |
| 2018/0181919 A1* | 6/2018 | Jobling ................... B60Q 3/47 |
| 2018/0222414 A1* | 8/2018 | Ihlenburg ........... B60H 1/00657 |
| 2019/0143936 A1* | 5/2019 | Abel Rayan ........... B60R 25/31 701/2 |

FOREIGN PATENT DOCUMENTS

| | | |
|---|---|---|
| EP | 3130511 B1 | 9/2018 |
| GB | 2524495 C | 4/2017 |

OTHER PUBLICATIONS

European Patent Office Communication, dated May 14, 2020, regarding Application No. 19155392.4, 10 pages.

* cited by examiner

FIG. 4

COMFORT CABIN STATES (400)

| STATE (402) | CRITERIA (404) | PASSENGER COMFORT PREFERNCES (406) |
|---|---|---|
| ARRIVAL (408) | UPON FIRST CONNECTION TO AIRCRAFT COMPUTER SYSTEM WHEN THE TIME IS NO MORE THAN 30 MINUTES PAST THE DEPARTURE TIME OF THE FLIGHT | PRESET DRINK ORDER, ARRIVAL LIGHT LEVEL SETTING, ARRIVAL VENTILATION LEVEL SETTING, ARRIVAL WINDOW TINT LEVEL SETTING, AND ARRIVAL SEAT POSITION SETTING |
| AWAKE (410) | HEART RATE WITHIN NORMAL RANGE | AWAKE LIGHT LEVEL SETTING, AWAKE VENTILATION LEVEL SETTING, AWAKE WINDOW TINT LEVEL SETTING. AND AWAKE SEAT POSITION SETTING |
| ANXIOUS (412) | HEART RATE EXCEEDS ANXIETY THRESHOLD, TEMPERATURE EXCEEDS ANXIOUS NORMAL TEMPERATURE THRESHOLD, ACCELEROMETER DETECTS FIDGETY MOTIONS | ANXIOUS TEMPERATURE SETTING, ANXIOUS SEAT POSITION SETTING, AND ANXIOUS LIGHT SETTING |
| SLEEPING (414) | HEART RATE FALLS BELOW SLEEPING THRESHOLD. ACCELEROMETER DETECTS LITTLE TO NO MOTION | SLEEPING WINDOW TINT LEVEL SETTING, SLEEPING LIGHT LEVEL SETTING, AND SLEEPING SEAT POSITION SETTING |
| AWAY FROM SEAT (416) | ACCELEROMETER RECOGNIZES STEPS. HEART RATE EXCEEDS RESTING THRESHOLD. NEAR FIELD COMMUNICATIONS CONNECTION IS LOST | NO SETTING CHANGES |
| DEPLANING (418) | AFTER FLIGHT HAS LANDED. ACCELEROMETER DETECTS STEPS | REQUEST DEPLANING INFORMATION |
| DISTRESS (420) | HEART RATE EXCEEDS DISTRESS THRESHOLD. NO HEART RATE. TEMPERATURE EXCEEDS NORMAL TEMPERATURE THRESHOLD. RAPID, ERRATIC MOTIONS | CALL FLIGHT ATTENDANT FOR HELP |
| HOT (422) | TEMPERATURE ABOVE PASSENGER SET LEVEL | HOT WINDOW TINT LEVEL SETTING AND HOT VENTILATION LEVEL SETTING |
| COLD (424) | TEMPERATURE BELOW PASSENGER SET LEVEL | COLD WINDOW TINT LEVEL SETTING AND COLD VENTILATION LEVEL SETTING |
| CUSTOM PASSENGER (426) | PASSENGER CAN SET CRITERIA FOR CUSTOM STATE TRIGGER. CAN BE AUTOMATICALLY ENTERED OR MANUALLY TRIGGERED | PASSENGER PRESET |

PASSENGER COMFORT SYSTEM

BACKGROUND INFORMATION

1. Field

The present disclosure relates generally to aircraft and, in particular, to a method and system for passenger comfort in an aircraft.

2. Background

Providing passenger comfort is an important goal with airline travel. Passenger comfort can be measured in a number of different ways. For example, passenger comfort includes different aspects, such as seat pitch, seat size, the adjustability of a seat, inflight entertainment, internet access, food service, and environmental controls.

One manner in which passenger comfort can be increased is through personalizing the passenger experience. For example, on some flights, personalized service from attendants can be provided. Further, a passenger may be provided personalized movie selections based on personal preferences for the passenger. Internet access also may be available. However, one aspect, such as the aircraft cabin environment, is static and allows for limited changes. As a result, personalizing the aircraft cabin environment for individual passengers may be more difficult than desired.

Therefore, it would be desirable to have a method and apparatus that take into account at least some of the issues discussed above, as well as other possible issues. For example, it would be desirable to have a method and apparatus that overcome a technical problem with increasing passenger comfort in an aircraft.

SUMMARY

An embodiment of the present disclosure provides a passenger vehicle comfort control apparatus comprising a passenger mobile device and a passenger comfort application running on the passenger mobile device. The passenger comfort application receives at least heart rate measurements from a sensor system; detects a current state of a passenger; and receives from a vehicle computer system passenger comfort preferences made by the passenger that are associated with different current states for the passenger. The passenger comfort application communicates one or more of the passenger comfort preferences saved in the passenger mobile device that correspond to a detected current state to the vehicle computer system over a wireless communications link. The vehicle computer system implements communicated passenger comfort preferences thereby enabling an increase in passenger comfort for the passenger in a vehicle.

Another embodiment of the present disclosure provides a passenger vehicle comfort control system comprising a vehicle computer system in a vehicle, a near-field communications reader for a passenger seat in the vehicle, and a comfort controller running on the vehicle computer system. The near-field communications reader facilitates connecting a passenger mobile device for a passenger with the vehicle computer system and registering the passenger mobile device with the passenger seat for which the passenger or the passenger mobile device is associated. The passenger mobile device communicates with a sensor system that measures at least heart rate for the passenger and identifies a current state of the passenger using at least heart rate measurements received from the sensor system. The comfort controller is configured to communicate passenger comfort preferences made by the passenger to the passenger mobile device in which the passenger mobile device associates the passenger comfort preferences with a detected current state of the passenger, and the comfort controller is configured to receive a number of passenger comfort preferences for the passenger for the current state of the passenger from the passenger mobile device and send a number of signals to a number of vehicle systems to adjust an environment for the passenger seat. The number of passenger comfort preferences is for a particular state in a number of states in which the particular state corresponds to the current state identified for the passenger from the heart rate measurements.

Yet another embodiment of the present disclosure provides a method for managing passenger comfort. A passenger mobile device is connected with a vehicle computer system in a vehicle using a near-field communications reader for a passenger seat in the vehicle for a passenger. Passenger comfort preferences associated with the passenger seat are identified by the vehicle computer system based on changes made to an environment in the vehicle by the passenger. Passenger comfort preferences made to the environment by the passenger are sent from the vehicle computer system to the passenger mobile device, which are associated with different current states for the passenger based on at least a heart rate for the passenger. A number of new passenger comfort preferences are received by the vehicle computer system from the passenger mobile device when the passenger mobile device detects a change in a current state of the passenger. A number of signals are sent by the vehicle computer system to a number of vehicle systems to change the environment for the passenger using the number of new passenger comfort preferences, enabling an increase in the passenger comfort in the vehicle.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 4 is an illustration of states and associated adjustments in accordance with an illustrative embodiment;

DETAILED DESCRIPTION

Figure 1:
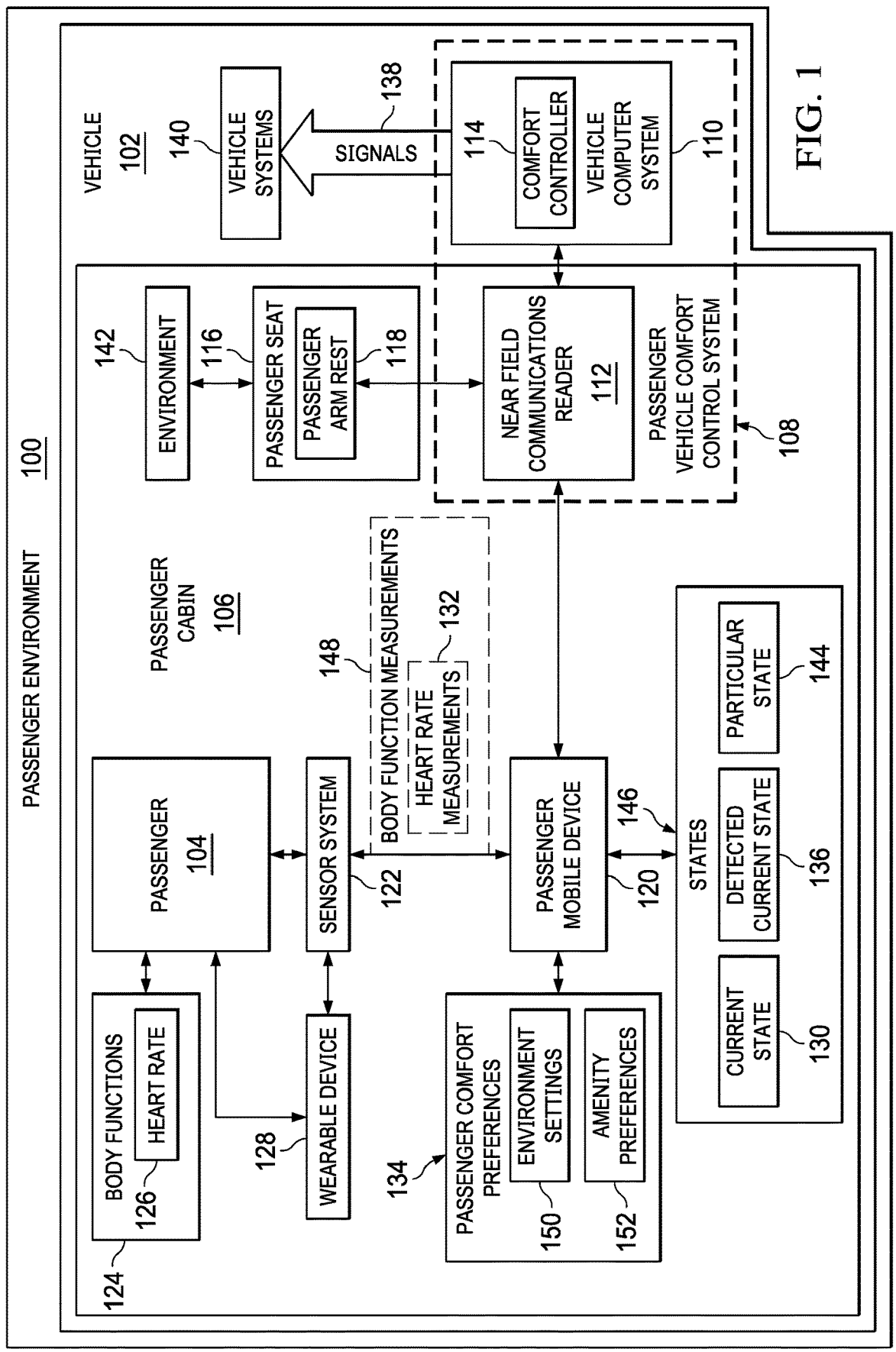
FIG. 1 is an illustration of a block diagram of a passenger environment in accordance with an illustrative embodiment.

The illustrative embodiments recognize and take into account one or more different considerations. For example, the illustrative embodiments recognize and take into account that passenger comfort can be increased by helping passengers to relax in the passenger cabin of a vehicle. For example, the illustrative embodiments recognize and take into account that environmental changes and other preferences for a passenger can be implemented automatically by detecting a state of a passenger. For example, the illustrative embodiments recognize and take into account that a light level, a window tint level, a temperature for a passenger seat, an airflow, and other environmental conditions can be automatically adjusted based on the current state of the passenger.

For example, the illustrative embodiments recognize and take into account that when the passenger is in a sleeping state, the light level for the passenger seat can be dimmed, the window tint level can be increased to reduce light, and the seat back for the passenger seat can be lowered. The illustrative embodiments also recognize and take into account that it would be desirable to make these adjustments to meet the preferences of each passenger in the sleeping state.

Thus, the illustrative embodiments provide a method, apparatus, and system for managing passenger comfort. In the illustrative examples, sensors are used to make measurements for the passenger. These measurements include at least a heart rate for the passenger. In one illustrative example, a passenger vehicle comfort system operates to increase passenger comfort in a passenger cabin in a vehicle.

The passenger vehicle comfort control system comprises a vehicle computer system in a vehicle, a near-field communications reader for a passenger seat in the vehicle, and a comfort controller running on the vehicle computer system. The near-field communications reader facilitates connecting a passenger mobile device for a passenger with the vehicle computer system and registering the passenger mobile device with the passenger seat for which the passenger or mobile passenger device is associated. The passenger mobile device communicates with a sensor system that measures at least the heart rate for the passenger and identifies the current state of the passenger using at least heart rate measurements received from the sensor system.

The comfort controller is configured to communicate passenger comfort preferences made by the passenger to the passenger mobile device, and the passenger mobile device associates the passenger comfort preferences with a detected current state of the passenger. The comfort controller is configured to receive a number of passenger comfort preferences for the passenger for the current state of the passenger from the passenger mobile device and send a number of signals to a number of vehicle systems to adjust an environment for the passenger seat based on the number of preferences for a particular state in the number of states in which the particular state corresponds to the current state identified for the passenger from body function measurements.

As used herein, "a number of," when used with reference items, means one or more items. For example, a number of passenger comfort preferences is one or more comfort preferences.

With reference now to the figures and, in particular, with reference to FIG. 1, an illustration of a block diagram of a passenger environment is depicted in accordance with an illustrative embodiment. As depicted, passenger environment 100 is an environment in which vehicle 102 operates. In this illustrative example, vehicle 102 takes a number of different forms. For example, vehicle 102 can be selected from a group comprising a mobile platform, an aircraft, a commercial aircraft, a rotorcraft, a surface ship, a train, a spacecraft, a submarine, a bus, an automobile, or some other suitable type of vehicle that is configured to carry one or more passengers.

As depicted, vehicle 102 carries passenger 104 in passenger cabin 106. In the illustrative example, vehicle 102 includes passenger vehicle comfort control system 108 that operates to increase comfort for passenger 104. Passenger vehicle comfort control system 108 comprises vehicle computer system 110, near-field communications reader 112, and comfort controller 114.

Vehicle computer system 110 is located in vehicle 102 and is a physical hardware system in vehicle 102 that includes one or more data processing systems. When more than one data processing system is present, those data processing systems are in communication with each other using a communications medium. The communications medium may be a network. The data processing systems may be selected from at least one of a computer, a server computer, a tablet, or some other suitable data processing system.

As used herein, the phrase "at least one of," when used with a list of items, means different combinations of one or more of the listed items may be used, and only one of each item in the list may be needed. In other words, "at least one of" means any combination of items and number of items may be used from the list, but not all of the items in the list are required. The item may be a particular object, a thing, or a category.

For example, without limitation, "at least one of item A, item B, or item C" may include item A, item A and item B, or item B. This example also may include item A, item B, and item C; or item B and item C. Of course, any combinations of these items may be present. In some illustrative examples, "at least one of" may be, for example, without limitation, two of item A, one of item B, and ten of item C; four of item B and seven of item C; or other suitable combinations.

Near-field communications reader 112 is for passenger seat 116 in vehicle 102. In one illustrative example, near-field communications reader 112 is located in passenger arm rest 118 for passenger seat 116.

As depicted, passenger 104 has passenger mobile device 120. Passenger mobile device 120 is a hardware device that has a size and weight that can be carried by passenger 104. Passenger mobile device 120 is a data processing system selected from a group comprising a mobile phone, a table computer, a smart watch, or some other suitable mobile data processing system.

Passenger mobile device 120 can communicate with near-field communications reader 112 using near-field communications. Near-field communications comprise a set of protocols that enable two electronic devices to establish communications by bringing the electronic devices within proximity of each other, such as near-field communications reader 112 and passenger mobile device 120. This proximity can be, for example, about four centimeters in some illustrative examples. As depicted, near-field communications can include different technologies, including localized Bluetooth. The type of near-field communications technology used in near-field communications reader 112 can be selected such that passenger mobile device 120 communicates with near-field communications reader 112 when passenger mobile device 120 is located in passenger seat 116. In other words, the distance for near-field communications may be set such that passenger mobile device 120 communicates with near-field communications reader 112 for passenger seat 116 and not near-field communications readers for other passenger seats at the same time. Further, the correct passenger seat can be verified by passenger 104.

As depicted, near-field communications reader 112 facilitates connecting passenger mobile device 120 with vehicle computer system 110 and registering passenger mobile device 120 with passenger seat 116 for which passenger 104 or passenger mobile device 120 is associated. In other words, the registration with passenger seat 116 allows vehicle computer system 110 to associate at least one of passenger 104 or passenger mobile device 120 with passenger seat 116.

Passenger mobile device 120 and vehicle computer system 110 communicate with each other in this example. This communication can occur by establishing a communications link with or without near-field communications reader 112 being part of the communications link.

The communication can occur using at least one of Wi-Fi communications, Bluetooth communications, near-field communications, or some other type of wireless communication. Wi-Fi is a trademark of Wi-Fi Alliance. Bluetooth is a trademark of the Bluetooth Special Interest Group. The communication can also comprise transferring data between passenger mobile device 120 and vehicle computer system 110 using near-field communications.

In this illustrative example, sensor system 122 measures body functions 124 for passenger 104. As depicted, passenger mobile device 120 also communicates with sensor system 122 and receives at least heart rate measurements 132 from sensor system 122. Heart rate measurements 132 is an example of body function measurements 148 received from sensor system 122 measuring body functions 124.

As depicted, body functions 124 includes at least heart rate 126 for passenger 104. However, other types of body functions can be measured in addition to heart rate 126. For example, body functions 124 can also include vital signs, which are pulse rate, temperature, respiration rate, and blood pressure. Of course, additional body functions can be measured in addition to or in place of vital signs. Additional body functions include, for example, an oxygen level, a blood glucose level, a perspiration level, or some other suitable body function.

Sensor system 122 can be located in wearable device 128 or passenger mobile device 120. In this illustrative example, wearable device 128 can be selected from one of a bracelet, a snap bracelet, a fitness wristband, an activity tracker, or some other suitable device. Passenger mobile device 120 can take a number of different forms. For example, passenger mobile device 120 can be a mobile phone, a smart watch, a tablet computer, smart glasses, or some other suitable passenger mobile device.

In this illustrative example, sensor system 122 includes an optical heart rate sensor. Sensor system 122 also can include at least one of a 3-axis accelerometer, an altimeter, a vibration monitor, a blood-oxygen sensor, or some other suitable type of sensor.

Further, passenger mobile device 120 identifies current state 130 of passenger 104 using at least heart rate measurements 132 received from sensor system 122. Current state 130 can be identified by using additional body function measurements, such as a respiratory rate, a blood pressure, an oxygen level, a blood glucose level, a perspiration level, a body temperature, or some other suitable body function measurement.

In the illustrative example, vehicle computer system 110 can adjust passenger environment 100 using comfort controller 114 running on vehicle computer system 110. As depicted, comfort controller 114 sends signals 138 to a number of vehicle systems 140. In this example, the number of vehicle systems 140 is selected from at least one of an environmental system, a window tint system, a seat controller system, a lighting system, a meal-ordering system, a flight entertainment system, an attendant messaging system, or some other vehicle system.

As depicted, passenger mobile device 120 can send passenger comfort preferences 134 in the form of environment settings 150. Environment settings 150 are settings for vehicle systems 140 and can include, for example, environment settings 150, which include at least one of a light level setting, a ventilation level setting, and a window tint level setting that are made by passenger 104.

As depicted, comfort controller 114 is configured to receive passenger comfort preferences 134 for passenger 104 for current state 130 of passenger 104 from passenger mobile device 120. In response to receiving passenger comfort preferences 134, such as environment settings 150, comfort controller 114 sends a number of signals 138 to the number of vehicle systems 140 to adjust environment 142 for passenger seat 116.

A number of passenger comfort preferences 134 are for particular state 144 in a number of states 146. As depicted, particular state 144 corresponds to current state 130 identified for passenger 104 from body function measurements 148 received from sensor system 122.

Passenger comfort preferences 134 can also include other types of preferences in addition to or in place of environment settings 150. For example, passenger comfort preferences 134 also can include amenity preferences 152. Amenity preferences 152 can include at least one of a drink selection, a movie selection, a blanket, a pillow, a meal selection, a service, or some other amenity for passenger 104.

In this illustrative example, passenger 104 can make changes to environment 142. The changes can be made by manipulating buttons, switches, or other types of controls. For example, passenger 104 can change an environmental setting that dims or brightens a light. As another example, passenger 104 can change a ventilation setting by increasing airflow through a vent for passenger seat 116.

Comfort controller 114 can detect changes made by passenger 104 to environment 142 for passenger seat 116. For example, comfort controller 114 can detect changes made by passenger 104 to settings, such as a light level setting, a ventilation level setting, a window tint level setting, a temperature setting, or other settings that can be adjusted by passenger 104 for environment 142 for passenger seat 116.

In this illustrative example, comfort controller 114 in vehicle computer system 110 communicates passenger comfort preferences 134 to passenger mobile device 120 based on changes made by passenger 104 to environment settings 150. Passenger mobile device 120 associates these received preferences with detected current state 136 for passenger 104.

Passenger mobile device 120 stores the passenger-adjusted settings in environment settings 150. For example, passenger mobile device 120 stores the passenger-adjusted settings in environment settings 150 associated with at least a detected awake state and a detected sleeping state in states 146 based on whether heart rate 126 for passenger 104 is above or below a preset level. In a similar fashion, vehicle computer system 110 can communicate passenger comfort preferences 134 based on amenity preferences 152 made by passenger 104.

While passenger 104 is in vehicle 102, passenger mobile device 120 can detect current state 130 for passenger 104 using sensor system 122. Current state 130 can be for passenger 104 in passenger seat 116 or in some other location within passenger cabin 106. Based on detected current state 136 of passenger 104, passenger mobile device 120 sends vehicle computer system 110 saved passenger-adjusted settings or saved amenity preferences associated with at least one of an awake state or a sleeping state. These passenger-adjusted settings include one or more of a light level setting, a ventilation level setting, and a window tint level setting, and vehicle computer system 110 adjusts at least one of a light level, a ventilation level, and a window tint level associated with passenger seat 116 for passenger 104.

In one illustrative example, one or more technical solutions are present that overcome a technical problem with improving passenger comfort in a vehicle, such as an aircraft. For example, in one illustrative example, passenger comfort is improved in vehicle 102, in the form of a commercial aircraft, in which vehicle computer system 110 is an aircraft computer system configured to control one or more of a light level, a ventilation level, and a window tint level associated with a passenger seat of a passenger. As a result, one or more technical solutions may provide a technical effect of increasing passenger comfort in vehicle 102 through automatically adjusting environment 142 for passenger 104 in passenger seat 116 based on passenger comfort preferences 134 for passenger 104 and detecting current state 130 for passenger 104.

As a result, at least one of vehicle computer system 110 or passenger mobile device 120 operates as a special-purpose computer system in which at least one of vehicle computer system 110 or passenger mobile device 120 enables increasing passenger comfort in vehicle 102. In particular, the process for automatically detecting passenger states and adjusting the environment for a passenger transforms one of vehicle computer system 110 or passenger mobile device 120 into a special-purpose computer system, as compared to currently available general-purpose computer systems that do not have these processes.

Figure 2:
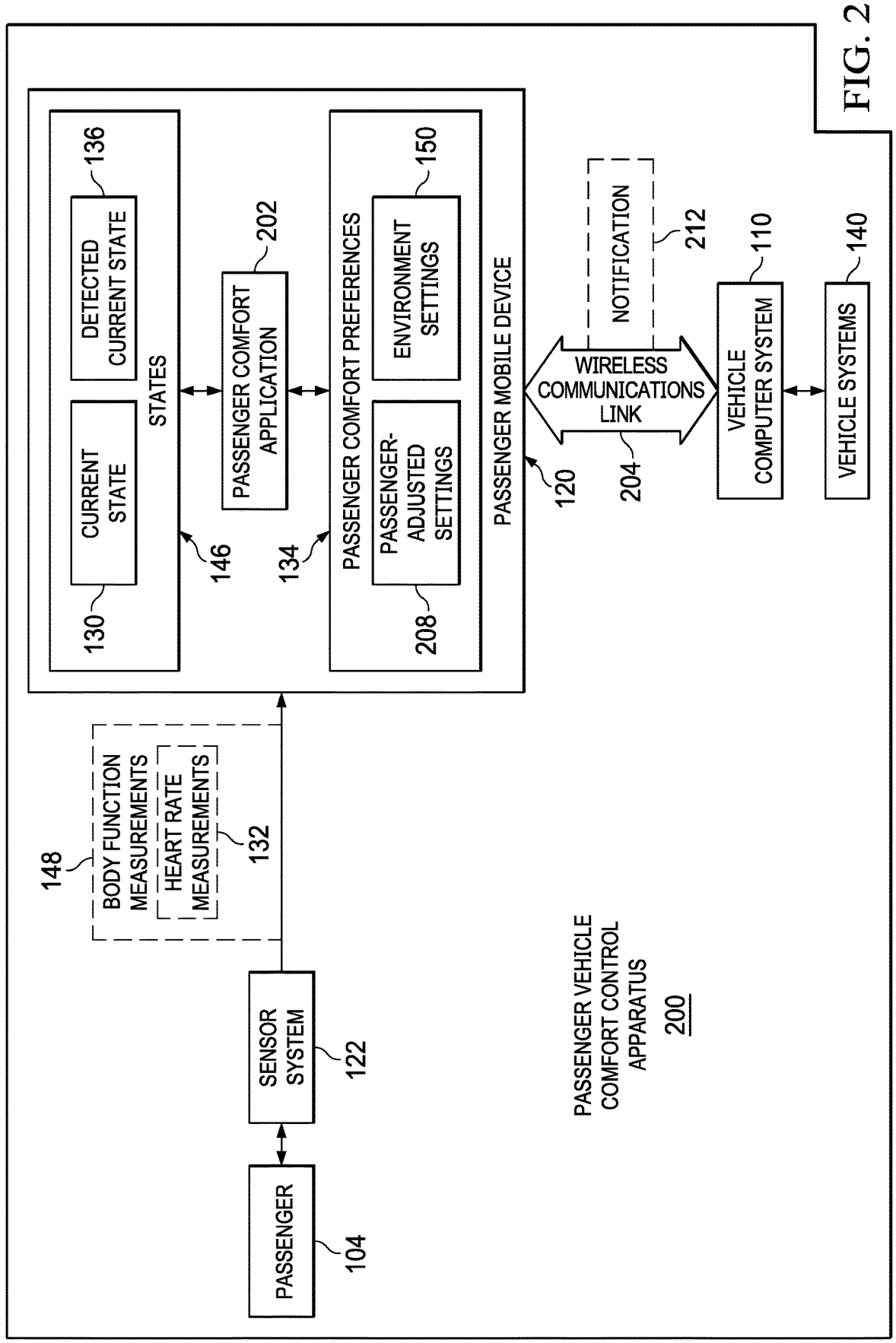
FIG. 2 is an illustration of a block diagram of a passenger vehicle comfort control apparatus in accordance with an illustrative embodiment.

Turning now to FIG. 2, an illustration of a block diagram of a passenger vehicle comfort control apparatus is depicted in accordance with an illustrative embodiment. In the illustrative examples, the same reference numeral may be used in more than one figure. This reuse of a reference numeral in different figures represents the same element in the different figures.

In this illustrative example, passenger vehicle comfort control apparatus 200 includes a number of different components. As depicted, passenger vehicle comfort control apparatus 200 comprises passenger mobile device 120, passenger comfort application 202, and sensor system 122.

As depicted, passenger comfort application 202 runs on passenger mobile device 120 and detects states 146 for passenger 104. For example, passenger comfort application 202 receives at least heart rate measurements 132 from sensor system 122 and detects current state 130 of passenger 104 in states 146. Passenger comfort application 202 also receives, from vehicle computer system 110, passenger comfort preferences 134 made by passenger 104 that are associated with different current states for passenger 104. Passenger comfort application 202 communicates one or more passenger comfort preferences 134 saved in passenger mobile device 120 that correspond to detected current state 136 to vehicle computer system 110 over wireless communications link 204, whereby vehicle computer system 110 implements communicated passenger comfort preferences thereby enabling an increase in passenger comfort for passenger 104 in vehicle 102 shown in block form in FIG. 1.

Passenger comfort application 202 is configured to detect current state 130 of passenger 104 from states 146 using at least one of heart rate measurements 132 received from sensor system 122. States 146 can include at least one of an awake state or a sleeping state based on whether heart rate 126, shown in block form in FIG. 1, is above or below a preset level.

In the illustrative example, passenger comfort application 202 receives passenger comfort preferences 134 from vehicle computer system 110. Passenger comfort preferences 134 include passenger-adjusted settings 208, which are adjustments to environment settings 150 for different vehicle systems in vehicle 102 made by passenger 104. For example, environment settings 150 include at least one of a light level setting, a ventilation level setting, and a window tint level setting. Passenger comfort preferences 134 can also include amenity preferences 152 shown in block form in FIG. 1.

Passenger comfort application 202 stores passenger-adjusted settings 208 as passenger comfort preferences 134 in association with at least a detected awake state or a detected sleeping state in states 146. In this manner, passenger comfort application 202 can send one or more of passenger comfort preferences 134 to vehicle computer system 110 to change environment 142 for passenger 104 in vehicle 102 shown in block form in FIG. 1.

These passenger comfort preferences are automatically communicated by passenger comfort application 202 to vehicle computer system 110 in response to detecting current state 130 of passenger 104. For example, passenger comfort application 202 can communicate saved passenger-adjusted settings in passenger comfort preferences 134 associated with at least one of an awake state or a sleeping state.

As depicted, passenger comfort preferences 134 can be at least one of a light level setting, a ventilation level setting, and a window tint level setting to cause the vehicle to adjust at least one of a light level, a ventilation level, and a window tint level associated with a passenger's seat. Passenger comfort preferences 134 can also include at least one of an amenity preference, a drink selection, a movie selection, a meal selection, or some other preference for passenger 104.

Further, passenger comfort application 202 can provide increased safety for passenger 104. In this manner, passenger comfort application 202 is configured to send notification 212 when body function measurements 148 indicate that passenger 104 is in a distress state. Notification 212 can be sent to vehicle computer system 110. Notification 212 can be a message, a text, or a signal to an attendant system in vehicle systems 140.

For example, passenger comfort application 202 can be configured to detect a distress state. In this illustrative example, the distress state can be detected based on at least one of a heart rate or a temperature exceeding a preset threshold. The preset threshold can be set, for example, using at least one of user input, a heart rate based on an age, a body fat level, an exercise history, a patient history, or other factors. In response to detecting the distress state, passenger comfort application 202 communicates notification 212 to vehicle computer system 110 that passenger 104 is in the distress state.

The illustration of passenger environment 100 and the different components in FIG. 1 and passenger vehicle comfort control apparatus 200 in FIG. 2 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, sensor system 122 may not be a part of passenger vehicle comfort control apparatus 200 in some implementations. In another illustrative example, passenger vehicle comfort control system 108 can also include at least one of passenger mobile device 120 or sensor system 122 as shown in block form in FIG. 1.

Figure 3:
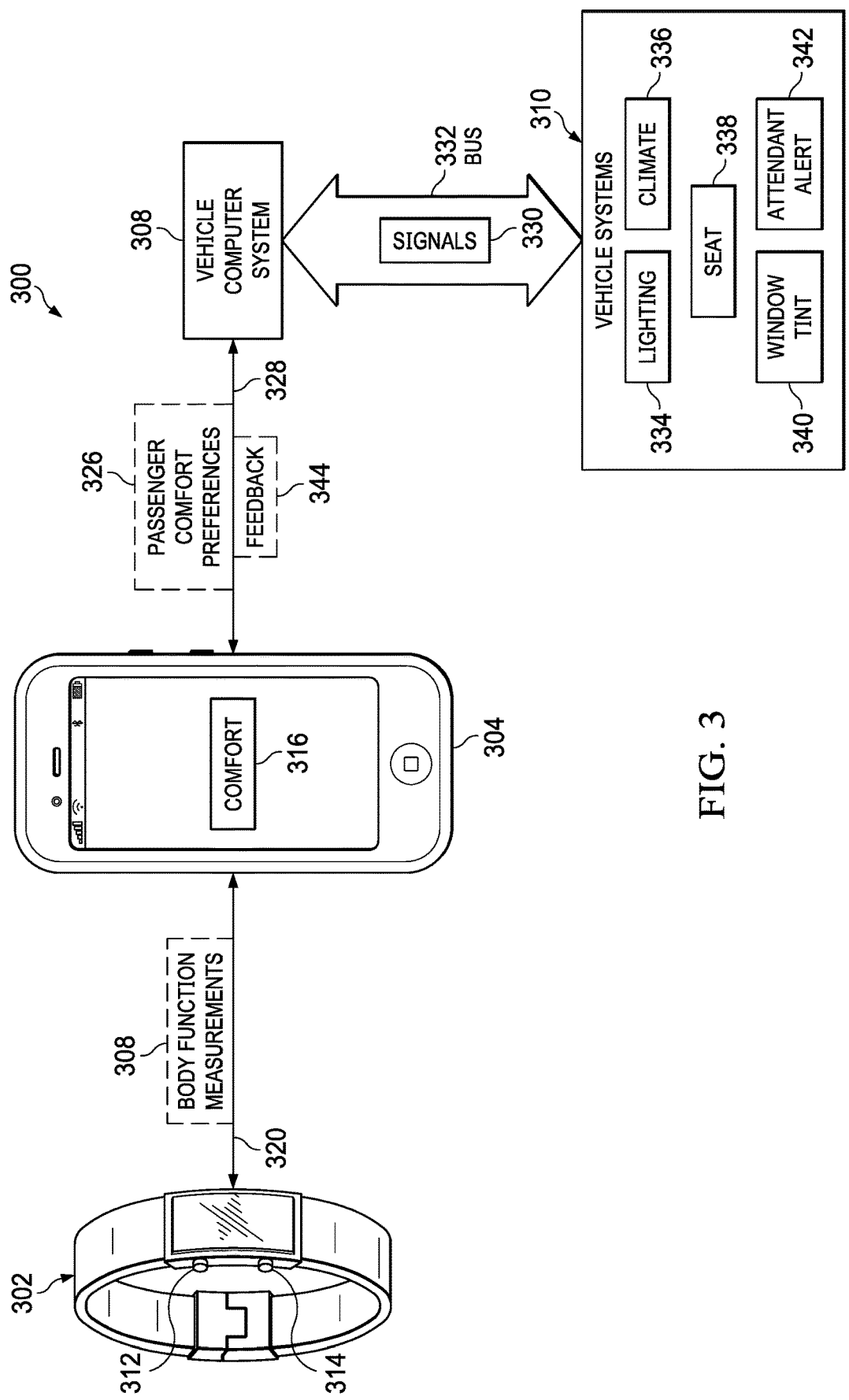
FIG. 3 is an illustration of a passenger vehicle comfort control system in accordance with an illustrative embodiment.

With reference now to FIG. 3, an illustration of a passenger vehicle comfort control system is depicted in accordance with an illustrative embodiment. As depicted, passenger vehicle comfort control system 300 includes activity tracker 302, mobile phone 304, vehicle computer system 308, and vehicle systems 310.

In this illustrative example, activity tracker 302 is an example of one implementation for wearable device 128, as shown in block form in FIG. 1, containing a sensor system. In this illustrative example, activity tracker 302 includes heart rate sensor 312 and temperature sensor 314. Activity tracker 302 is configured to communicate with mobile phone 304 using wireless communications link 320, such as a Bluetooth communications link. Activity tracker 302 may be provided to the passenger as a disposable, wearable device. For example, activity tracker 302 sends body function measurements 322 to mobile phone 304 over wireless communications link 320.

Mobile phone 304 is an example of passenger mobile device 120 in FIG. 1. Passenger comfort application 316 runs on mobile phone 304. Passenger comfort application 316 can be downloaded as an application by a passenger from an app store or an app marketplace. Passenger comfort application 316 stores passenger comfort preferences and criteria for different states and receives measurements from activity tracker 302. Based on comparing the criteria to the measurements, passenger comfort application 316 identifies the current state for the passenger.

In response to detecting a current state, passenger comfort application 316 sends passenger comfort preferences 326 associated with the current state identified to vehicle computer system 308 over wireless communications link 328. In this illustrative example, wireless communications link 328 can be a Wi-Fi communications link, a Bluetooth communications link, an optical communications link, or some other suitable type of wireless communications link.

Vehicle computer system 308 sends signals 330 over bus 332 to vehicle systems 310. Signals 330 are selected to cause one or more of vehicle systems 310 to effect changes in the environment or provide amenities to the passenger.

As depicted, vehicle systems 310 include, for example, lighting 334, climate 336, seat 338, window tint 340, and attendant alert 342. Lighting 334 controls overhead lighting for the different passenger seats. Climate 336 controls heating and cooling systems in the passenger seats. Additionally, climate 336 controls ventilation for each of the passenger seats. Window tint 340 controls the window tint level for passenger windows. Attendant alert 342 controls an alert system for attendants to indicate which seats require attention.

As depicted, vehicle computer system 308 also may return feedback 344 to passenger comfort application 316 over wireless communications link 328. This feedback may provide a log of actions performed by vehicle computer system 308 in response to receiving passenger comfort preferences. Additionally, feedback 344 also may include passenger comfort preferences 326 based on changes made by input from the passenger. This input may involve the passenger manipulating controls in the passenger cabin. These updated passenger comfort preferences can be used to update desired preferences of the passenger for particular states while traveling in the vehicle.

This type of process can be performed automatically to adjust the environment for the passenger. In this manner, the automatic adjustments of the environment reduce the efforts needed by the passenger to have a comfortable environment and desired amenities, thereby increasing passenger comfort.

With reference to FIG. 4, an illustration of states and associated adjustments is depicted in accordance with an illustrative embodiment. As depicted, table 400 depicts states that can be detected by a passenger mobile device, such as states 146 and passenger mobile device 120 as shown in block form in FIG. 1 and FIG. 2.

As depicted in table 400, state column 402 contains states that can be detected for a passenger. The states in state column 402 are examples of states 146 in FIG. 1 and FIG. 2. Criteria column 404 in table 400 contains conditions for detecting a particular state for a passenger. Passenger comfort preferences column 406 identifies adjustments or amenities that can be made for the passenger. In this example, the different states and adjustments are for a vehicle that takes the form of an aircraft, such as a commercial jet airliner.

As depicted, row 408 is an arrival state, row 410 is an awake state, row 412 is an anxious state, row 414 is a sleeping state, row 416 is an away from seat state, row 418 is a deplaning state, row 420 is a distress state, row 422 is a hot state, row 424 is a cold state, and row 426 is a custom passenger state.

In row 408, the arrival state is considered to be present when a passenger first connects to the aircraft computer system in the aircraft while the time of connection is no more than 30 minutes past the departure time of the flight. This state results in a preset drink order, an arrival light level setting, an arrival ventilation level setting, an arrival window tint level setting, and an arrival seat position setting being sent as passenger comfort preferences to the aircraft computer system for use in adjusting the settings for the passenger when the arrival state is detected. In this example, the settings can be based on passenger adjustments as the passenger arrives when boarding the aircraft.

An awake state in row 410 is present when the heart rate for the passenger is within a normal range. The normal range can be selected based on the particular user. For example, age, activity level, and other factors may be taken into account in selecting the normal range for the heart rate.

In this example, passenger comfort preferences in the form of an awake light level setting, an awake ventilation level setting, an awake window tint level setting, and an awake seat position setting are sent to the aircraft computer system from the passenger mobile device. In one illustrative example, the settings are the same as for the arrival state in row 408.

The anxious state in row 412 is detected when the heart rate exceeds an anxiety threshold, the temperature exceeds a normal temperature threshold, or an accelerometer detects fidgety motions. In this state, passenger comfort preferences are an anxious temperature setting, an anxious seat position setting, and an anxious light level setting.

In row 414, the sleeping state is detected when the heart rate falls below a sleeping threshold and the accelerometer detects little or no motion from the passenger. In the sleeping state, the passenger comfort preferences are a sleeping window tint level setting, a sleeping light level setting, and a sleeping seat position setting. For example, the window tint level setting may be increased and a light level setting may be decreased as compared to when the passenger is in the awake state. A sleeping seat position setting may be a reclined position for the passengers.

In the away from seat state in row 416, no setting changes are made. The away from seat state can be detected when the accelerometer recognizes steps, the heart rate exceeds a resting threshold, and the near-field connection is lost.

The deplaning state in row 418 can be detected after the flight has landed and steps are detected by the accelerometer. In this example, the passenger comfort preferences comprise requesting deplaning information. As depicted, deplaning information can be send to the mobile passenger device. The deplaning information includes at least one of a map or directions to a destination in an airport. The deplaning information can be for a connecting flight or for baggage. The directions provided can be active ones that give turn-by-turn directions as the passenger moves in the airport.

In row 420, a distress state is detected when the heart rate exceeds a distress threshold, or no heart rate is detected. The distress state can also be present when the temperature of the passenger exceeds a normal temperature threshold and rapid, erratic motions are present. In this state, the passenger comfort preferences are to call for attendant assistance.

The hot state in row 422 is detected when the temperature is above a passenger-set level. For example, the passenger may set a temperature of 74 degrees as being too warm. If the temperature reaches 74 degrees at the passenger seat, adjustments are made using passenger comfort preferences in row 422. These preferences include a hot window tint level setting and a hot ventilation level setting. The hot window tint level setting may make the windows entirely opaque and the hot ventilation level setting may increase the ventilation level to a preselected level for the passenger.

As depicted, in row 424, a cold state is present when the temperature is below a passenger-set level. When the cold state is detected, the passenger comfort preferences include a cold window tint level setting and a cold ventilation level setting. The cold window tint level setting reduces the opaqueness of the window tint level and the cold ventilation level setting reduces the ventilation in this particular example.

Additionally, a custom passenger state is present in row 426. The custom passenger state can be detected based on criteria set by the passenger in this custom state. The criteria can be automatically entered or manually triggered. In other words, the passenger can set the criteria in this state. Alternatively, the passenger can select the state to be entered by activating the state using an application, such as passenger comfort application 202 in FIG. 2 or passenger comfort application 316 in FIG. 3. The passenger comfort preferences can be preset for the passenger or can be custom passenger settings made from input from the passenger.

Thus, the number of states 146 in FIG. 1 can be selected from at least one of an awake state, an inactive state, a sleeping state, a hot state, a cold state, a distress state, an arrival state, a deplaning state, or a custom state as depicted in table 400. The number of states in states 146 in FIG. 1 can also be some other suitable state in place of or in addition to the states depicted in table 400.

The different states, conditions, and adjustments illustrated in table 400 are provide to illustrate one manner in which states and adjustments can be implemented. These illustrations are not meant to limit what states, conditions, or preferences can be used in other illustrative examples. For example, the states, criteria, and passenger comfort preferences may vary from the ones illustrated in table 400 in other implementations. For example, when a cold state in row 424 is detected, passenger comfort preferences for the cold state may also include increasing the temperature for the passenger seat when the passenger seat includes a heating and cooling feature.

Figure 5:
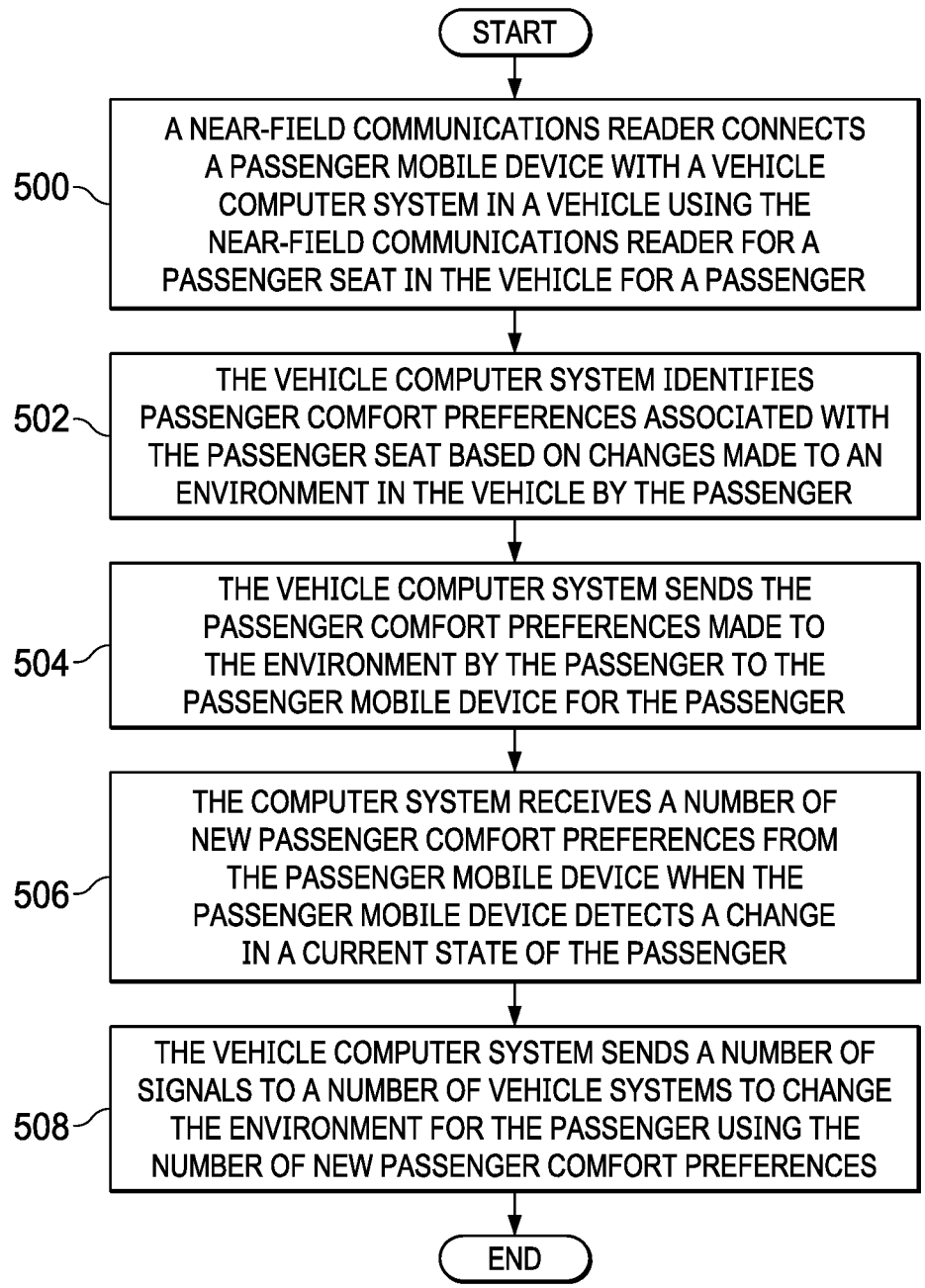
FIG. 5 is an illustration of a flowchart of a process for managing passenger comfort in accordance with an illustrative embodiment.

Turning next to FIG. 5, an illustration of a flowchart of a process for managing passenger comfort is depicted in accordance with an illustrative embodiment. The process illustrated in the flowchart in FIG. 5 can be implemented in vehicle 102 using passenger vehicle comfort control system 108 as shown in block form in FIG. 1. The different operations can be implemented using at least one of software or hardware. When software is used, the different operations can be implemented in program code that is run on a processor unit.

The process begins with a near-field communications reader connecting a passenger mobile device with a vehicle computer system in a vehicle using the near-field communications reader for a passenger seat in the vehicle for a passenger (operation 500). The vehicle computer system identifies passenger comfort preferences associated with the passenger seat based on changes made to an environment in the vehicle by the passenger (operation 502).

The vehicle computer system sends the passenger comfort preferences made to the environment by the passenger to the passenger mobile device for the passenger (operation 504). The passenger comfort preferences are associated with different current states for the passenger based on at least a heart rate for the passenger.

The computer system receives a number of new passenger comfort preferences from the passenger mobile device when the passenger mobile device detects a change in a current state of the passenger (operation 506). The vehicle computer system sends a number of signals to a number of vehicle systems to change the environment for the passenger using the number of new passenger comfort preferences (operation 508). The process terminates thereafter. The process in FIG. 5 enables an increase in passenger comfort in the vehicle.

Figure 6:
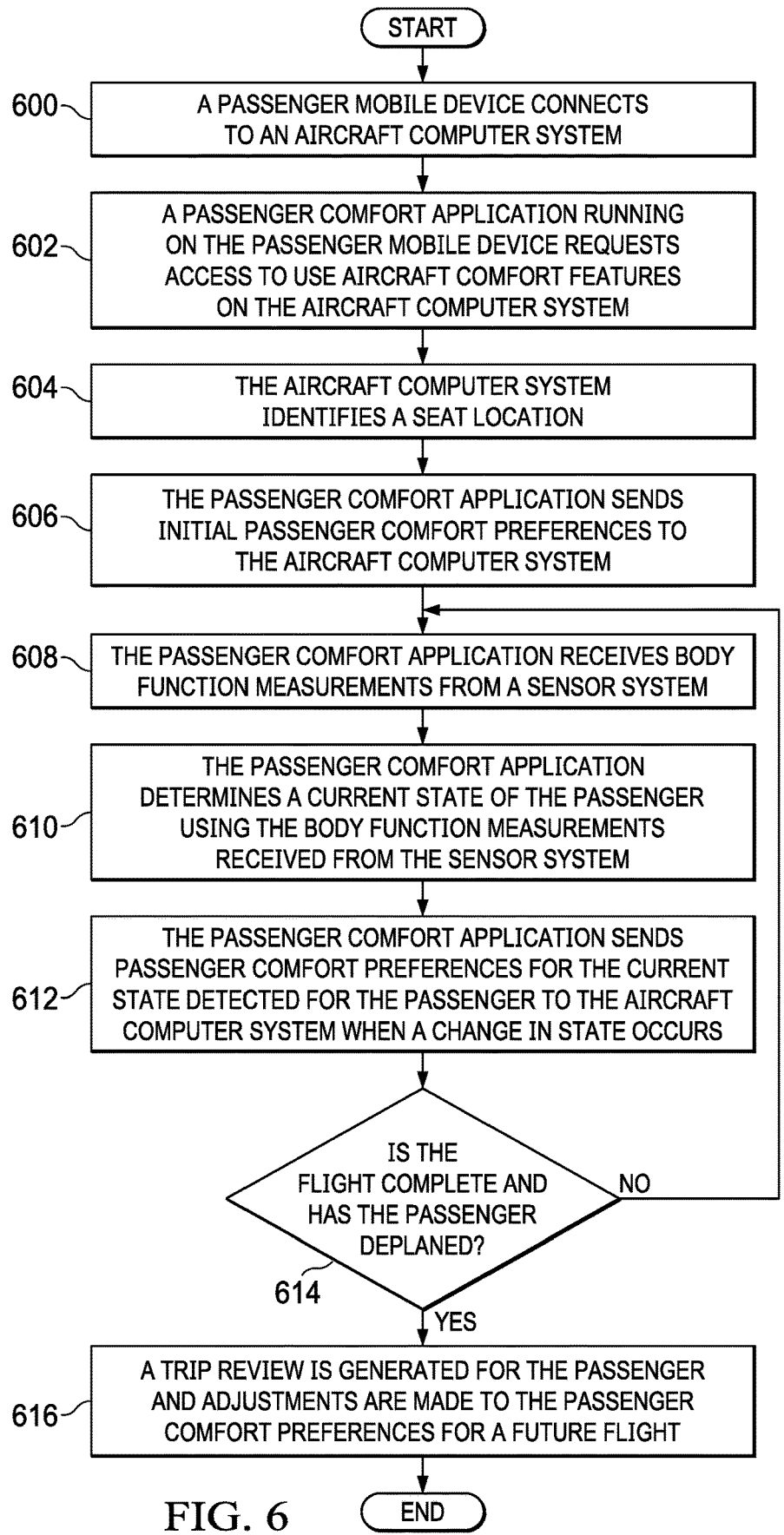
FIG. 6 is an illustration of a flowchart of a process for managing passenger comfort in an aircraft in accordance with an illustrative embodiment.

With reference next to FIG. 6, an illustration of a flowchart of a process for managing passenger comfort in an aircraft is depicted in accordance with an illustrative embodiment. The process illustrated in the flowchart in FIG. 6 can be implemented in vehicle 102 using passenger vehicle comfort control system 108 as shown in block form in FIG. 1. The different operations can be implemented using at least one of software or hardware in passenger mobile device 120 in FIG. 1 and FIG. 2. When software is used, the different operations can be implemented in program code that is run on a processor unit.

The process begins with a passenger mobile device connecting to an aircraft computer system (operation 600). This connection can be performed by the passenger mobile device being sufficiently close to a near-field communications reader in an arm rest for the passenger seat to establish a communications link. For example, the two devices may be sufficiently close to each other to communicate when the passenger is sitting in the passenger seat and is holding the passenger mobile device sufficiently close to the near-field communications reader.

A passenger comfort application running on the passenger mobile device requests access to use aircraft comfort features on the aircraft computer system (operation 602). As part of this request, the aircraft computer system identifies a seat location (operation 604). In operation 604, the seat location is where the mobile passenger device running the passenger comfort application is located. The seat location can be identified in a number of different ways. For example, when the passenger seat has a near-field communications reader, the seat location of the passenger seat is identified based on the near-field communications reader that has established communications with the passenger mobile device.

As another example, the passenger comfort application can send the passenger seat location or some other identifier that allows the aircraft computer system to identify the passenger seat and the location of the passenger. This information sent by the passenger comfort application can be received as input from the passenger entering the passenger seat information. In another illustrative example, the passenger comfort application can receive the passenger seat information from an airline reservation system.

The passenger comfort application sends initial passenger comfort preferences to the aircraft computer system (operation 606). These preferences are stored in the passenger mobile device and can be entered by the passenger or can be based on the passenger comfort preferences from prior flights.

The passenger comfort application receives body function measurements from a sensor system (operation 608). In this illustrative example, the sensor system can be a wearable device or integrated as part of the passenger mobile device. In operation 608, at least a heart rate for the passenger is monitored by the sensor system. Other body function measurements can be made including, for example, at least one of a respiratory rate, a blood pressure, an oxygen level, a blood glucose level, a perspiration level, a body temperature, or some other suitable body function measurement.

The passenger comfort application determines a current state of the passenger using the body function measurements received from the sensor system (operation 610). In this illustrative example, the identification of the current state can be performed using criteria, such as the criteria illustrated in criteria column 404 in table 400 in FIG. 4.

The passenger comfort application sends passenger comfort preferences for the current state detected for the passenger to the aircraft computer system when a change in state occurs (operation 612).

A determination is made as to whether the flight is complete and the passenger has deplaned (operation 614). If the flight is not complete and the passenger has not deplaned, the process returns to operation 608.

Otherwise, the process generates a trip review for the passenger and makes adjustments to the passenger comfort preferences for a future flight (operation 616). The process terminates thereafter. In this illustrative example, the trip review may be sent in an email. The trip review may outline vital signs during the trip, request feedback, provide suggestions, or other information. The adjustments for the passenger comfort preferences can be stored in the passenger mobile device or in a separate location of an account set up for the passenger.

Figure 7:
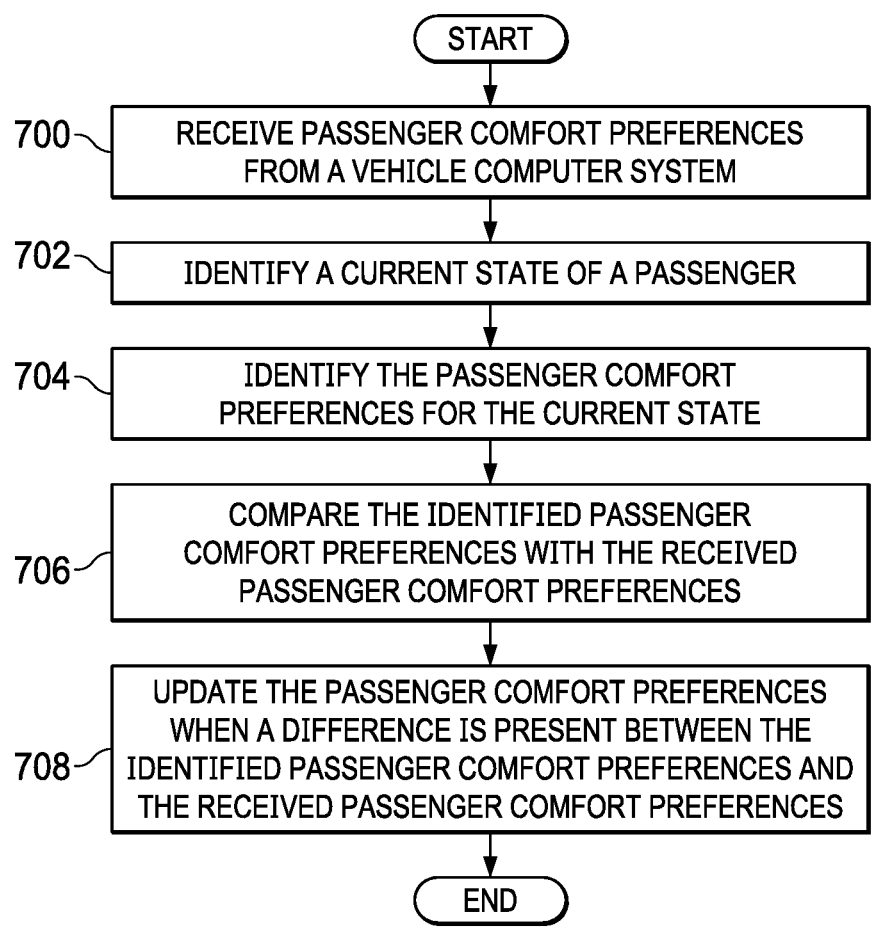
FIG. 7 is an illustration of a flowchart of a process for updating passenger comfort preferences in accordance with an illustrative embodiment.

With reference next to FIG. 7, an illustration of a flowchart of a process for updating passenger comfort preferences is depicted in accordance with an illustrative embodiment. The process illustrated in the flowchart in FIG. 7 can be implemented in passenger comfort application 202 running on passenger mobile device 120 shown in block form in FIG. 2. The different operations can be implemented using at least one of software or hardware. When software is used, the different operations can be implemented in program code that is run on a processor unit.

The process begins by receiving passenger comfort preferences from a vehicle computer system (operation 700). In this illustrative example, the passenger comfort preferences can be received in real-time. The process identifies a current state of a passenger (operation 702). The process identifies the passenger comfort preferences for the current state (operation 704). The process compares the identified passenger comfort preferences with the received passenger comfort preferences (operation 706). The process updates the passenger comfort preferences when a difference is present between the identified passenger comfort preferences and the received passenger comfort preferences (operation 708). The process terminates thereafter.

Figure 8:
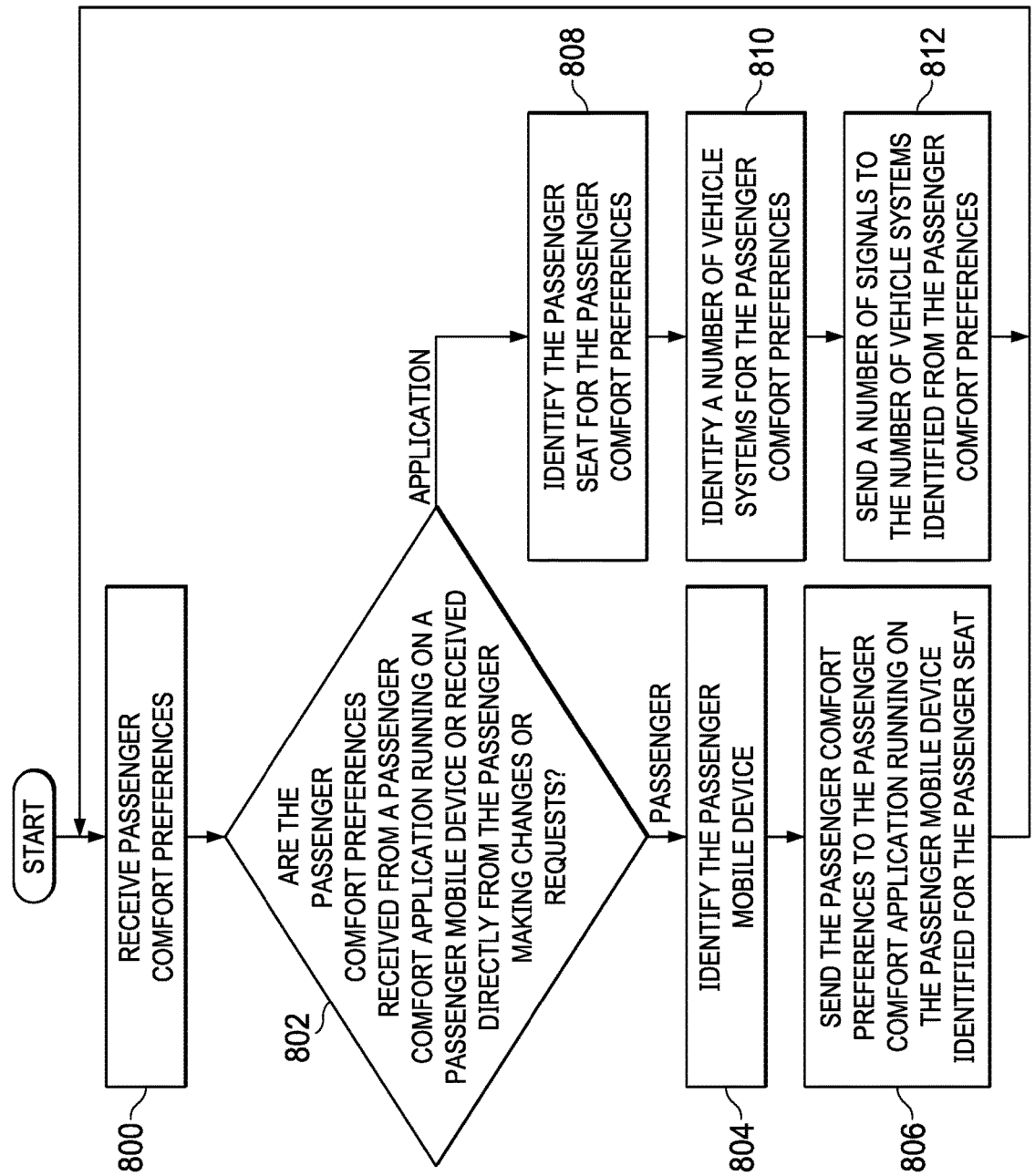
FIG. 8 is an illustration of a flowchart of a process for processing passenger comfort preferences in accordance with an illustrative embodiment.

With reference now to FIG. 8, an illustration of a flowchart of a process for processing passenger comfort preferences is depicted in accordance with an illustrative embodiment. The process illustrated in the flowchart in FIG. 8 can be implemented in vehicle 102 using passenger vehicle comfort control system 108 shown in block form in FIG. 1. For example, this process can be implemented by vehicle computer system 110 in FIG. 1. The different operations can be implemented using at least one of software or hardware. When software is used, the different operations can be implemented in program code that is run on a processor unit.

The process begins by receiving passenger comfort preferences (operation 800). These preferences can be received from a passenger comfort application running on a passenger mobile device or directly from the passenger making changes or requests.

A determination is made as to whether the passenger comfort preferences are received from a passenger comfort application running on a passenger mobile device or received directly from the passenger making changes or requests (operation 802). If the passenger comfort preferences are made by the passenger, the process identifies the passenger mobile device (operation 804). For example, the passenger comfort preferences can be made by the passenger manipulating switches or controls for settings such as a light level, a window tint level, a seat position, a temperature, a ventilation level, or other controls. These controls are associated with the passenger seat in the illustrative examples. With this information, the vehicle computer system can identify the passenger mobile device that is registered to the passenger seat.

The process then sends the passenger comfort preferences to the passenger comfort application running on the passenger mobile device identified for the passenger seat (operation 806). The process returns to operation 800. In this manner, feedback can be provided to update the passenger comfort preferences stored on the passenger mobile device during the current trip in the vehicle.

With reference again to operation 802, if the passenger comfort preferences are received from a passenger comfort application running on a passenger mobile device, the process identifies the passenger seat for the passenger comfort preferences (operation 808).

The process identifies a number of vehicle systems for the passenger comfort preferences (operation 810). For example, if the passenger comfort preferences include a light level setting, the process identifies the lighting system in the vehicle. As another example, if the passenger comfort preferences include a window tint level, the process identifies the window system for the vehicle.

The process sends a number of signals to the number of vehicle systems identified from the passenger comfort preferences (operation 812). The process returns to operation 800. These signals can include at least one of commands, data, or other information. The signals are sent to cause the vehicle systems to make adjustments based on the passenger comfort preferences received from the passenger comfort application.

The flowcharts and block diagrams in the different depicted embodiments illustrate the architecture, functionality, and operation of some possible implementations of apparatuses and methods in an illustrative embodiment. In this regard, each block in the flowcharts or block diagrams can represent at least one of a module, a segment, a function, or a portion of an operation or step. For example, one or more of the blocks can be implemented as program code, hardware, or a combination of program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware. Each block in the flowcharts or the block diagrams may be implemented using special-purpose hardware systems that perform the different operations or combinations of special-purpose hardware and program code run by the special-purpose hardware.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in the flowcharts or block diagrams.

Figure 9:
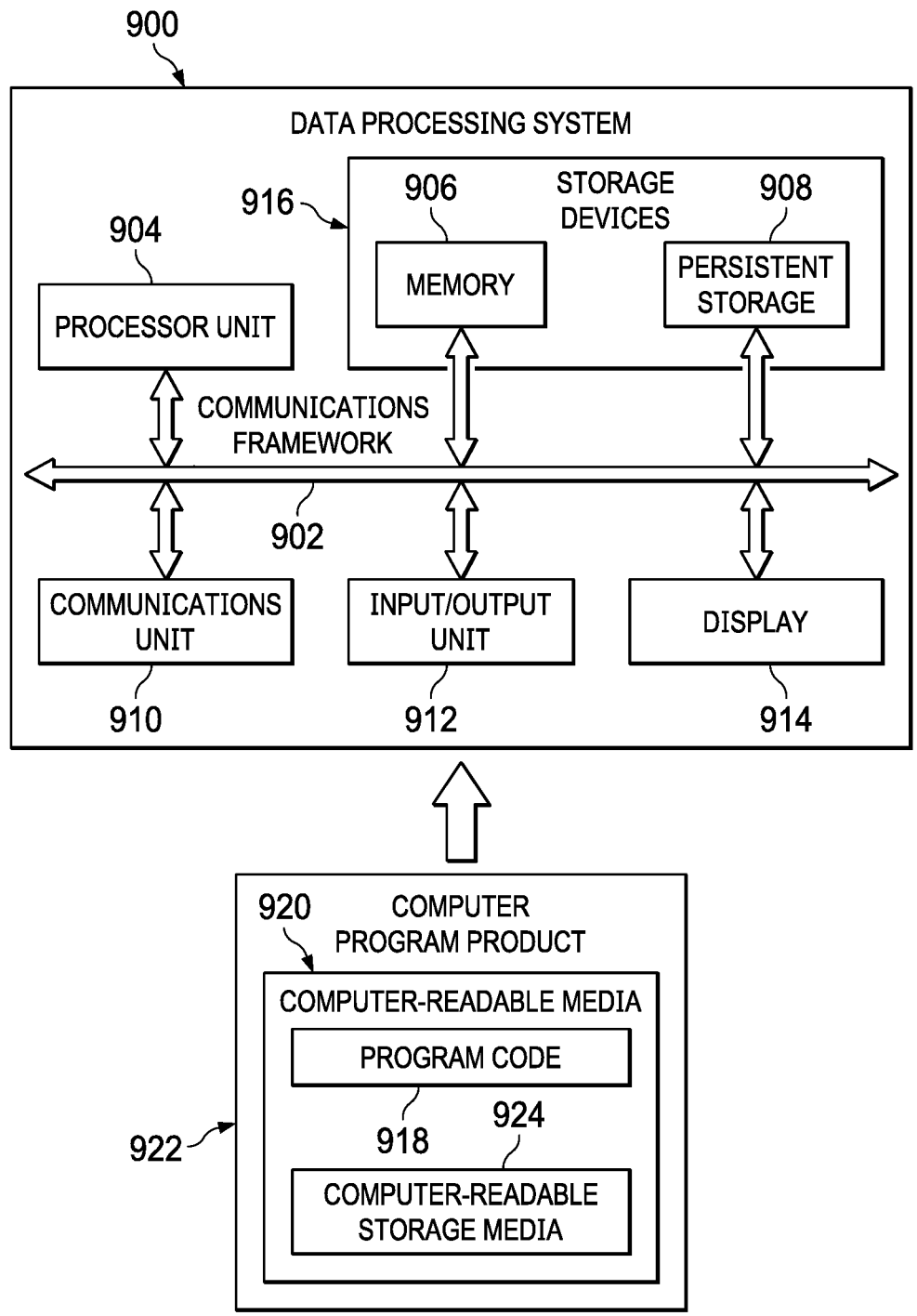
FIG. 9 is an illustration of a block diagram of a data processing system in accordance with an illustrative embodiment.

Turning now to FIG. 9, an illustration of a block diagram of a data processing system is depicted in accordance with an illustrative embodiment. Data processing system 900 may be used to implement vehicle computer system 110 and passenger mobile device 120 in FIG. 1. In this illustrative example, data processing system 900 includes communications framework 902, which provides communications between processor unit 904, memory 906, persistent storage 908, communications unit 910, input/output unit 912, and display 914. In this example, communications framework 902 may take the form of a bus system.

Processor unit 904 serves to execute instructions for software that may be loaded into memory 906. Processor unit 904 may be a number of processors, a multi-processor core, or some other type of processor, depending on the particular implementation.

Memory 906 and persistent storage 908 are examples of storage devices 916. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 916 also may be referred to as computer-readable storage devices in these illustrative examples. Memory 906, in these examples, may be, for example, a random-access memory or any other suitable volatile or non-volatile storage device. Persistent storage 908 may take various forms, depending on the particular implementation.

For example, persistent storage 908 may contain one or more components or devices. For example, persistent storage 908 may be a hard drive, a solid-state drive, a flash memory, a rewritable optical disk, a rewritable magnetic tape, or some combination of the above. The media used by persistent storage 908 also may be removable. For example, a removable hard drive may be used for persistent storage 908.

Communications unit 910, in these illustrative examples, provides for communications with other data processing systems or devices. In these illustrative examples, communications unit 910 is a network interface card.

Input/output unit 912 allows for input and output of data with other devices that may be connected to data processing system 900. For example, input/output unit 912 may provide a connection for user input through at least one of a keyboard, a mouse, or some other suitable input device. Further, input/output unit 912 may send output to a printer. Display 914 provides a mechanism to display information to a user.

Instructions for at least one of the operating system, applications, or programs may be located in storage devices 916, which are in communication with processor unit 904 through communications framework 902. The processes of the different embodiments may be performed by processor unit 904 using computer-implemented instructions, which may be located in a memory, such as memory 906.

These instructions are referred to as program code, computer-usable program code, or computer-readable program code that may be read and executed by a processor in processor unit 904. The program code in the different embodiments may be embodied on different physical or computer-readable storage media, such as memory 906 or persistent storage 908.

Program code 918 is located in a functional form on computer-readable media 920 that is selectively removable and may be loaded onto or transferred to data processing system 900 for execution by processor unit 904. Program code 918 and computer-readable media 920 form computer program product 922 in these illustrative examples. In the illustrative example, computer-readable media 920 is computer-readable storage media 924. In these illustrative examples, computer-readable storage media 924 is a physical or tangible storage device used to store program code 918 rather than a medium that propagates or transmits program code 918.

Alternatively, program code 918 may be transferred to data processing system 900 using a computer-readable signal media. The computer-readable signal media may be, for example, a propagated data signal containing program code 918. For example, the computer-readable signal media may be at least one of an electromagnetic signal, an optical signal, or any other suitable type of signal. These signals may be transmitted over at least one of communications links, such as wireless communications links, optical fiber cable, coaxial cable, a wire, or any other suitable type of communications link.

The different components illustrated for data processing system 900 are not meant to provide architectural limitations to the manner in which different embodiments may be implemented. The different illustrative embodiments may be implemented in a data processing system including components in addition to or in place of those illustrated for data processing system 900. Other components shown in FIG. 9 can be varied from the illustrative examples shown. The different embodiments may be implemented using any hardware device or system capable of running program code 918.

Figure 10:
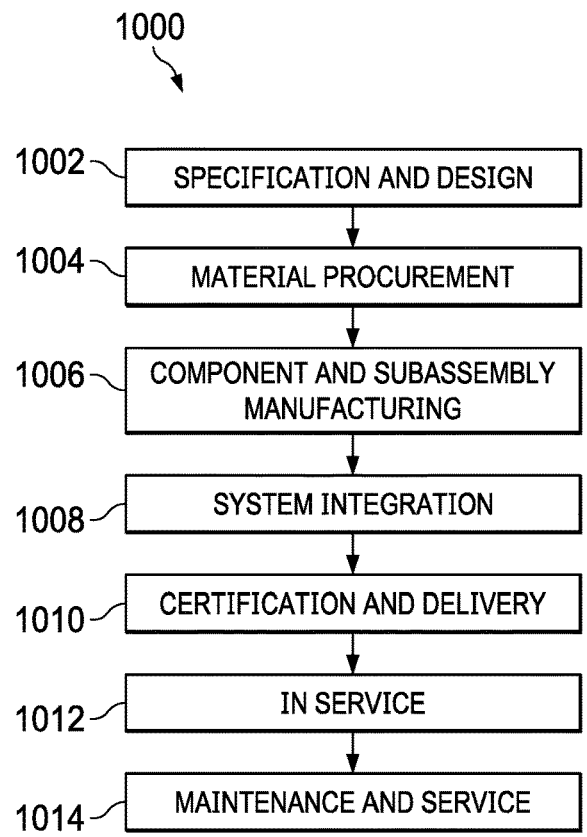
FIG. 10 is an illustration of a block diagram of an aircraft manufacturing and service method in accordance with an illustrative embodiment.
Figure 11:
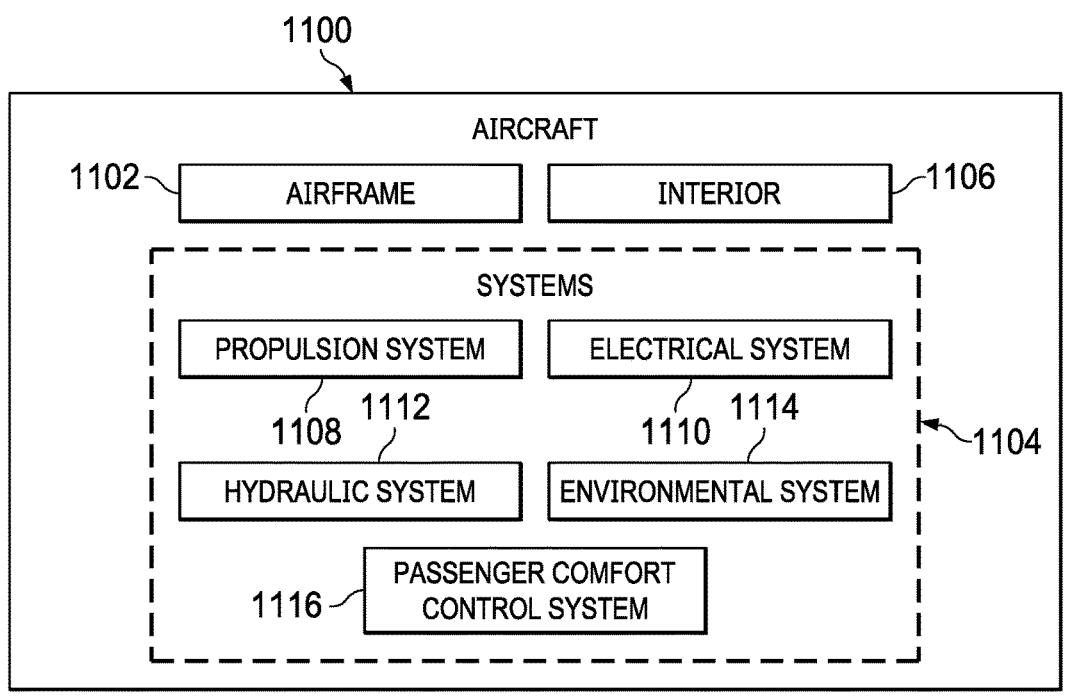
FIG. 11 is an illustration of a block diagram of an aircraft in which an illustrative embodiment may be implemented.

Next, illustrative embodiments of the disclosure may be described in the context of aircraft manufacturing and service method 1000 as shown in FIG. 10 and aircraft 1100 as shown in FIG. 11. Turning first to FIG. 10, an illustration of a block diagram of an aircraft manufacturing and service method is depicted in accordance with an illustrative embodiment. During pre-production, aircraft manufacturing and service method 1000 may include specification and design 1002 of aircraft 1100 in FIG. 11 and material procurement 1004.

During production, component and subassembly manufacturing 1006 and system integration 1008 of aircraft 1100 in FIG. 11 takes place. Thereafter, aircraft 1100 in FIG. 11 may go through certification and delivery 1010 in order to be placed in service 1012. While in service 1012 by a customer, aircraft 1100 in FIG. 11 is scheduled for routine maintenance and service 1014, which may include modification, reconfiguration, refurbishment, and other maintenance or service.

Each of the processes of aircraft manufacturing and service method 1000 may be performed or carried out by a system integrator, a third party, an operator, or some combination thereof. In these examples, the operator may be a customer. For the purposes of this description, a system integrator may include, without limitation, any number of aircraft manufacturers and major-system subcontractors; a third party may include, without limitation, any number of vendors, subcontractors, and suppliers; and an operator may be an airline, a leasing company, a military entity, a service organization, and so on.

With reference now to FIG. 11, an illustration of a block diagram of an aircraft is depicted in which an illustrative embodiment may be implemented. In this example, aircraft 1100 is produced by aircraft manufacturing and service method 1000 in FIG. 10 and may include airframe 1102 with a plurality of systems 1104 and interior 1106. Examples of systems 1104 include one or more of propulsion system 1108, electrical system 1110, hydraulic system 1112, environmental system 1114, and passenger comfort control system 1116. In this illustrative example, passenger comfort control system 1116 can be implemented in aircraft 1100 using passenger vehicle comfort control system 108 as illustrated in FIG. 1. Any number of other systems may be included. Although an aerospace example is shown, different illustrative embodiments may be applied to other industries, such as the automotive industry.

Apparatuses and methods embodied herein may be employed during at least one of the stages of aircraft manufacturing and service method 1000 in FIG. 10.

In one illustrative example, components or subassemblies produced in component and subassembly manufacturing 1006 in FIG. 10 may be fabricated or manufactured in a manner similar to components or subassemblies produced while aircraft 1100 is in service 1012 in FIG. 10. As yet another example, one or more apparatus embodiments, method embodiments, or a combination thereof may be utilized during production stages, such as component and subassembly manufacturing 1006 and system integration 1008 in FIG. 10.

One or more apparatus embodiments, method embodiments, or a combination thereof may be utilized while aircraft 1100 is in service 1012, during maintenance and service 1014 in FIG. 10, or both. For example, passenger vehicle comfort control system 108 in FIG. 1 can be used to operate passenger comfort control system 1116 in FIG. 11 to enable an increase in the comfort level for passengers of aircraft 1100 while aircraft 1100 is in service 1012.

As another example, passenger vehicle comfort control system 108 in FIG. 1 can be implemented in aircraft 1100 as passenger comfort control system 1116 during maintenance and service 1014. This implementation can be performed during at least one of modification, reconfiguration, refurbishment, and other maintenance or service for aircraft 1100. The use of a number of the different illustrative embodiments may substantially expedite the assembly of aircraft 1100, reduce the cost of aircraft 1100, or both expedite the assembly of aircraft 1100 and reduce the cost of aircraft 1100.

Thus, the illustrative embodiments provide a method, apparatus, and system for managing passenger comfort preferences in vehicles. The different illustrative examples provide an ability to increase passenger comfort in vehicles, such as aircraft. In one illustrative example, a sensor system monitors body functions for a passenger. Based on the state identified using the measurements received from the sensor system, passenger comfort preferences associated with the detected states are sent to a vehicle computer system. For example, if the measurements indicate that the passenger is hot, the passenger comfort preferences for a hot state can be sent to the vehicle computer system to change the environment for the passenger. For example, the passenger comfort preferences, such as a ventilation setting or any temperature setting, can be sent to the computer system. The settings may increase the ventilation and reduce the temperature for the passenger.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component may be configured to perform the action or operation described. For example, the component may have a configuration or design for a structure that provides the component an ability to perform the action or operation that is described in the illustrative examples as being performed by the component.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A passenger vehicle comfort control apparatus comprising:
   a passenger mobile device; and
   a passenger comfort application running on the passenger mobile device, wherein the passenger comfort application receives at least heart rate measurements from a sensor system; detects a current state of a passenger; and communicates one or more stored passenger comfort preferences saved in the passenger mobile device that correspond to the detected current state of the passenger to a vehicle computer system over a wireless communications link, whereby the vehicle computer system implements the communicated stored passenger comfort preferences thereby enabling an increase in passenger comfort for the passenger in a vehicle;
   wherein the passenger comfort application receives feedback from the vehicle computer system relating to detected passenger-adjusted passenger comfort preferences made by the passenger and wherein the passenger comfort application compares the passenger-adjusted passenger comfort preferences with the stored passenger comfort preferences for an identified state and updates the stored passenger comfort preferences for the identified state when a difference is present.

2. The passenger vehicle comfort control apparatus of claim 1 further comprising:
   the sensor system in communication with the passenger mobile device, wherein the sensor system measures at least a heart rate for the passenger.

3. The passenger vehicle comfort control apparatus of claim 1, wherein the passenger comfort application receives at least the heart rate measurements from the sensor system and is configured to detect the current state of the passenger as at least an awake state and a sleeping state based on whether a heart rate is above or below a preset level.

4. The passenger vehicle comfort control apparatus of claim 3, wherein the passenger comfort application receives the passenger-adjusted passenger comfort preferences from the vehicle computer system, wherein the passenger-adjusted passenger comfort preferences comprise environment settings including at least one of a light level setting, a ventilation level setting, or a window tint level setting that are made by the passenger, and the passenger comfort application stores passenger-adjusted settings in association with at least a detected awake state and a detected sleeping state.

5. The passenger vehicle comfort control apparatus of claim 4, wherein based on the detected current state of the passenger, the passenger comfort application communicates to the vehicle computer system the stored passenger-adjusted settings associated with at least one of the awake state or the sleeping state, which includes one or more of the light level setting, the ventilation level setting, and the window tint level setting, to thereby cause the vehicle to adjust at least one of a light level, a ventilation level, or a window tint level associated with a passenger seat for the passenger.

6. The passenger vehicle comfort control apparatus of claim 5, wherein the vehicle is a commercial passenger aircraft and the vehicle computer system is an aircraft computer system configured to control one or more of the light level, the ventilation level, and the window tint level associated with the passenger seat for the passenger.

7. The passenger vehicle comfort control apparatus of claim 1, wherein the passenger comfort preferences include at least one of a light level setting, a ventilation level setting, a seat position setting, a window tint level setting, an amenity preference, a drink selection, a movie selection, or a meal selection.

8. The passenger vehicle comfort control apparatus of claim 2, wherein the sensor system measures at least the heart rate for the passenger and additionally measures body functions that are selected from at least one of a respiratory rate, a blood pressure, a blood glucose level, a perspiration level, or a body temperature.

9. The passenger vehicle comfort control apparatus of claim 1, wherein a number of the different detected current states is selected from at least one of an awake state, an inactive state, a sleeping state, a hot state, a cold state, a distress state, an arrival state, or a deplaning state.

10. The passenger vehicle comfort control apparatus of claim 9, wherein the passenger comfort application detects the distress state based on at least one of a heart rate or a temperature exceeding a preset threshold, and in response to a detected distress state, the passenger comfort application communicates a notification to the vehicle computer system that the passenger is in the distress state.

11. The passenger vehicle comfort control apparatus of claim 2, wherein the sensor system is located in a wearable device.

12. The passenger vehicle comfort control apparatus of claim 1, wherein the passenger comfort application is configured to send a distress alert when body function measurements indicate that the passenger is in a distress state.

13. A passenger vehicle comfort control system comprising:
   a vehicle computer system in a vehicle;
   a near-field communications reader for a passenger seat in the vehicle, wherein the near-field communications reader facilitates connecting a passenger mobile device for a passenger with the vehicle computer system and registering the passenger mobile device with the passenger seat for which the passenger or the passenger mobile device is associated, wherein the passenger mobile device communicates with a sensor system that measures at least a heart rate for the passenger and identifies a current state of the passenger using at least heart rate measurements received from the sensor system; and
   a comfort controller running on the vehicle computer system, wherein the comfort controller is configured to communicate passenger-adjusted passenger comfort preferences made by the passenger to the passenger mobile device in which the passenger mobile device associates the passenger-adjusted passenger comfort preferences with a detected current state of the passenger, and the comfort controller is configured to receive a number of stored passenger comfort preferences for the passenger for the current state of the passenger from the passenger mobile device and send a number of signals to a number of vehicle systems to adjust an environment for the passenger seat, wherein the number of passenger comfort preferences is for a particular state in a number of states in which the particular state corresponds to the current state identified for the passenger from the heart rate measurements and wherein the passenger comfort application compares the passenger-adjusted passenger comfort preferences with the stored passenger comfort preferences for the detected current state and updates the stored passenger comfort preferences for the detected current state when a difference is present.

14. The passenger vehicle comfort control system of claim 13, wherein the vehicle computer system communicates the passenger-adjusted passenger comfort preferences to the passenger mobile device, wherein the passenger-adjusted passenger comfort preferences include at least one of a light level setting, a ventilation level setting, or a window tint level setting that are made by the passenger, whereby the passenger mobile device stores passenger-adjusted settings associated with at least a detected awake state and a detected sleeping state based on whether the heart rate for the passenger is above or below a preset level.

15. The passenger vehicle comfort control system of claim 14, wherein based on the detected current state of the passenger, the vehicle computer system receives from the passenger mobile device the stored passenger-adjusted settings associated with at least one of an awake state or a sleeping state, which include one or more of the light level setting, the ventilation level setting, and the window tint level setting, and the vehicle computer system adjusts at least one of a light level, a ventilation level, or a window tint level associated with the passenger seat for the passenger.

16. The passenger vehicle comfort control system of claim 15, wherein the vehicle is a commercial aircraft and the vehicle computer system is an aircraft computer system configured to control one or more of the light level, the ventilation level, and the window tint level associated with the passenger seat for the passenger.

17. The passenger vehicle comfort control system of claim 13, wherein the near-field communications reader is located in a passenger arm rest for the passenger seat.

18. The passenger vehicle comfort control system of claim 13, wherein the comfort controller sends the number of signals to the number of vehicle systems selected from at least one of an environmental system, a window tint system, a seat controller system, a lighting system, a meal-ordering system, a flight entertainment system, or an attendant messaging system.

19. The passenger vehicle comfort control system of claim 13, wherein the comfort controller is configured to detect when the passenger is in a deplaning state and send deplaning information to the passenger mobile device in which the deplaning information includes at least one of a map or directions to a destination in an airport.

20. The passenger vehicle comfort control system of claim 13, wherein the passenger comfort preferences include at least one of a light level setting, a ventilation level setting, a seat position setting, a window tint level setting, an amenity preference, a drink selection, a movie selection, or a meal selection.

21. The passenger vehicle comfort control system of claim 13, wherein body function measurements used to identify the current state of the passenger are selected from at least one of the heart rate, a respiratory rate, a blood pressure, a blood glucose level, a perspiration level, or a body temperature.

22. The passenger vehicle comfort control system of claim 13, wherein the number of states is selected from at least one of an awake state, an inactive state, a sleeping state, a hot state, a cold state, a distress state, an arrival state, or a deplaning state.

23. The passenger vehicle comfort control system of claim 13, wherein the sensor system is located in the passenger mobile device.

24. The passenger vehicle comfort control system of claim 13, wherein the sensor system is located in a wearable device.

25. The passenger vehicle comfort control system of claim 13, wherein the passenger mobile device is selected from a group comprising a mobile phone, a tablet computer, and a smart watch.

26. The passenger vehicle comfort control system of claim 13, wherein the vehicle is selected from a group comprising a mobile platform, an aircraft, a commercial aircraft, a rotorcraft, a surface ship, a train, a spacecraft, a submarine, a bus, and an automobile.

27. A method for managing passenger comfort, the method comprising:
connecting a passenger mobile device with a vehicle computer system in a vehicle using a near-field communications reader for a passenger seat in the vehicle for a passenger;
identifying, by the vehicle computer system, passenger-adjusted passenger comfort preferences associated with the passenger seat based on changes made to an environment in the vehicle by the passenger;
sending the passenger-adjusted passenger comfort preferences made to the environment by the passenger from the vehicle computer system to the passenger mobile device, which are associated with different current states for the passenger based on at least a heart rate of the passenger;
receiving, by the vehicle computer system, a number of stored passenger comfort preferences from the passenger mobile device when the passenger mobile device detects a change in a current state of the passenger;
sending, by the vehicle computer system, a number of signals to a number of vehicle systems to change the environment for the passenger using the number of new passenger comfort preferences, enabling an increase in the passenger comfort in the vehicle; and
comparing the passenger-adjusted passenger comfort preferences for an identified state with the number of stored passenger comfort preferences for the identified state and updating the stored passenger comfort preferences for the identified state when a difference is present.

28. The method of claim 27, wherein the number of vehicle systems is selected from at least one of an environmental system, a window tint system, a seat controller system, a lighting system, a meal-ordering system, a flight entertainment system, or an attendant messaging system.

* * * * *